United States Patent [19]
Forestier et al.

[11] Patent Number: 5,415,854
[45] Date of Patent: May 16, 1995

[54] COSMETIC USE OF BENZALMALONATE DIORGANOPOLYSILOXANES AND NOVEL COSMETIC COMPOSITIONS CONTAINING SUCH COMPOUNDS FOR THE PROTECTION OF SKIN AND HAIR

[75] Inventors: Serge Forestier, Claye-Souilly; Gerard Lang, Saint-Gratien; Herve Richard, Paris, all of France

[73] Assignee: L'Oreal, Paris, France

[21] Appl. No.: 81,064

[22] Filed: Jun. 22, 1993

Related U.S. Application Data

[63] Continuation of Ser. No. 777,487, Oct. 24, 1991, abandoned, which is a continuation of Ser. No. 479,384, Feb. 13, 1990, abandoned.

[30] Foreign Application Priority Data

Feb. 15, 1989 [FR] France .................. 89 01989

[51] Int. Cl.$^6$ .......................... A61K 7/42; A61K 7/06
[52] U.S. Cl. ........................... 424/59; 424/70.12; 424/47; 424/DIG. 5; 514/63; 514/937; 514/944
[58] Field of Search ............... 424/59, 60, 70, 71; 514/947, 938

[56] References Cited

U.S. PATENT DOCUMENTS

| | | |
|---|---|---|
| 4,405,469 | 9/1983 | Hafner et al. |
| 4,457,911 | 4/1984 | Connor ............ 424/59 |
| 4,696,969 | 9/1987 | Thimineur ........ 524/762 |
| 5,053,290 | 10/1991 | Canivenc ......... 428/429 |

FOREIGN PATENT DOCUMENTS

| | | | |
|---|---|---|---|
| 0100651 | 2/1984 | European Pat. Off. | A61K 7/42 |
| 0138321 | 4/1985 | European Pat. Off. | A61K 7/42 |
| 335777 | 10/1989 | European Pat. Off. | A61K 7/420 |

*Primary Examiner*—Thurman K. Page
*Assistant Examiner*—Sally Gardner
*Attorney, Agent, or Firm*—Marshall, O'Toole, Gerstein, Murray & Borun

[57] ABSTRACT

The cosmetic use is described, in particular for use as a UV filter, of benzalmalonate diorganopolysiloxanes having either formula:

$$B-\underset{\underset{R}{|}}{\overset{\overset{R}{|}}{Si}}-O-\left[\underset{\underset{R}{|}}{\overset{\overset{R}{|}}{Si}}-O\right]_r-\left[\underset{\underset{A}{|}}{\overset{\overset{R}{|}}{Si}}-O\right]_s-\underset{\underset{R}{|}}{\overset{\overset{R}{|}}{Si}}-B \quad (1)$$

where R is $C_1$-$C_{10}$ alkyl, phenyl or 3,3,3-trifluoropropyl, B is R or A, r=0-200, s=0-50, or formula:

$$\left[\underset{\underset{A}{|}}{\overset{\overset{R}{|}}{Si}}-O\right]_t\left[\underset{\underset{A}{|}}{\overset{\overset{R}{|}}{Si}}-O\right]_u \quad (2)$$

where u=1-20, t=0-20 and t+u≧3. A and/or B represent an alkylene or alkyleneoxy benzalmalonate which may be substituted.

13 Claims, No Drawings

COSMETIC USE OF BENZALMALONATE DIORGANOPOLYSILOXANES AND NOVEL COSMETIC COMPOSITIONS CONTAINING SUCH COMPOUNDS FOR THE PROTECTION OF SKIN AND HAIR

This is a Continuation of U.S. application Ser. No. 07/777,487, filed Oct. 24, 1991; in turn a Continuation of Serial No. 07/479,384, filed Feb. 13, 1990, both now abandoned.

The present invention concerns the cosmetic use of benzalmalonate diorganopolysiloxanes, particularly as UV filters, as well as novel cosmetic compositions containing such compounds for the protection of skin and hair.

Light of wavelengths between 280 nm and 400 nm is known to cause browning of the human epidermis; radiation of wavelengths between 280 nm and 320 nm known as UV-B causes erythema and cutaneous burns which may hinder the development of a tan; UV-B radiation must therefore be filtered out.

It is further known that UV-A radiation, with wavelengths between 320 nm and 400 nm, promotes browning of the skin and is likely to damage it, particularly with sensitive skin or where the skin is continually exposed to the sun's rays. In particular, UV-A radiation causes loss of skin elasticity and the appearance of lines resulting in premature ageing. It promotes the erythmatic reaction or amplifies it in some cases and may even be the cause of phototoxic or photallergenic reactions.

It is desirable therefore to design UV absorbing compounds so that they absorb a wide band of UV radiation in order to filter out both UV-A and UV-B.

It is further known that constituents of cosmetic preparations do not always have sufficient light stability and degrade when exposed to light.

It is thus desirable to incorporate UV filtering compounds into such preparations. These filters must also be stable and have sufficient solubility in media normally used in cosmetics, in particular oils and fats.

With hair, it is also desirable to protect it against photochemical degradation, particularly discolouring or change of shade.

Grafting molecules having a UV filtering effect onto polymer chains such as synthetic carbon polymers, natural polymers, protein hydrolysates or polyaminoamides is also known. Graft polymers as described, for example, in French patents numbers 2 197 023, 2 237 912, 2 531 960, 2 548 018, 2 549 069, 2 586 692 and 2 586 693 may be used to prepare cosmetic compositions for protection of human skin or as sun screens. However, graft polymers generally have low solubility in the usual cosmetic solvents, particularly in oily supports, and they form films having too rigid a structure.

The applicant has now discovered that, surprisingly, certain benzalmalonate diorganopolysiloxanes have good cosmetic properties and good filtering properties over a wide range of wavelengths, from 280 nm to 360 nm. In particular they have excellent liposolubility and can thus be used in the fatty supports used in cosmetics. Apart from their good filtering powers and good solubility in oily media and the usual cosmetic solvents, these benzalmalonate diorganopolysiloxanes also have excellent chemical and photochemical stability and soften the skin and hair, which tolerate them well.

An object of the present invention is, then, the cosmetic use of benzalmalonate diorganopolysiloxanes, particularly as UV filtering agents for radiation of wavelengths between 280 nm and 360 nm, selected from those having the formula:

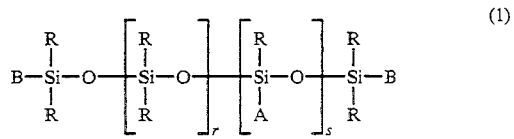

(1)

wherein:
R may be the same for each occurrence or different and is selected from $C_1$–$C_{10}$ alkyl radicals, phenyl radicals and 3,3,3-trifluoropropyl radicals, at least 80% by number of the R radicals being methyl radicals,
B may be the same for each occurrence or different and is selected from radicals R and A,
r is a number between 0 and 200 inclusive,
s is a number between 0 and 50 inclusive and if s is 0 at least one of the two B radicals is A; and from those having the formula:

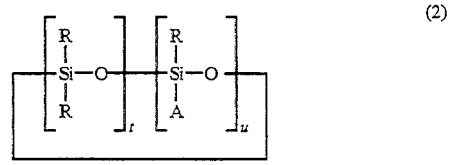

(2)

wherein:
R has the meaning defined for formula (1),
u is a number between 1 and 20 inclusive,
t is a number between 0 and 20 inclusive,
t+u is greater than or equal to 3; and wherein in both formulae the symbol A denotes a radical having the formula:

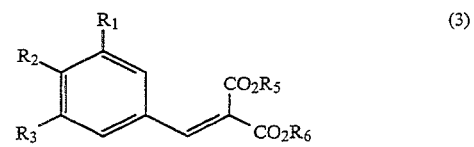

(3)

wherein:
$R_1$ and $R_2$ are selected from a hydrogen atom, a hydroxyl radical, a trimethylsiloxy radical, a $C_1$–$C_6$ alkyl radical, a $C_1$–$C_6$ alkoxy radical and a divalent group Y with the formula:

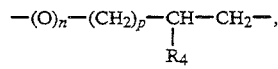

wherein:
n is 0 or 1, p is a whole number between 1 and 10 inclusive, preferably between 1 and 4, and $R_4$ is selected from a hydrogen atom and a $C_1$–$C_4$ alkyl radical, one of the two radicals $R_1$ and $R_2$ necessarily representing group Y,
$R_3$ represents a hydrogen atom, a $C_1$–$C_6$ alkyl radical or a $C_1$–$C_6$ alkoxy radical,
$R_5$ and $R_6$ may be identical or different and represent a $C_1$–$C_8$ alkyl radical.

In the above formulae the alkyl and alkoxy radicals may be linear or branched.

The following linear or branched $C_1$-$C_6$ alkoxy radicals merit particular mention: methoxy, ethoxy, n-propoxy, isopropoxy, n-butoxy, isobutoxy, tert-butoxy, n-amyloxy, isoamyloxy, neopentyloxy and n-hexyloxy.

The following linear or branched $C_1$-$C_6$ alkyl radicals merit particular mention: methyl, ethyl, n-propyl, isopropyl n-butyl, isobutyl, tert-butyl, n-amyl, isoamyl, neopentyl and n-hexyl, and the $C_1$-$C_8$ alkyl radicals may be the foregoing radicals or the n-heptyl, n-octyl, and 2-ethylhexyl radicals.

Preferred alkyl radicals R are methyl, ethyl, propyl, n-butyl, n-octyl and 2-ethylhexyl. Preferably at least 80% by number of the radicals are methyl.

Particularly preferred polymers are random or block polymers having the formula (1) or (2) with at least one of the following features:
R is methyl,
B is methyl,
$R_1$ is H or Y,
$R_2$ is Y, methoxy or butoxy,
$R_3$ is H or methoxy,
n=0 or 1,
p=1,
$R_4$ is H or methyl,
$R_5$ and $R_6$ are ethyl or 2-Ethylhexyl,
r is between 5 and 20 inclusive,
s is between 2 and 15 inclusive,
t+u is between 3 and 10 inclusive.

Preparation of polymers with formula (1) or (2) may start from the corresponding polymer wherein all the A radicals are hydrogen.

This polymer is denoted by SiH; SiH groups may be present within the chain and/or at its extremities. These SiH polymers are well known in the silicone industry and are generally commercially available.

They are described, for example, in American patents U.S. Pat. Nos. 3,220,972, 3,436,366, 3,697,473 and 4,340,709.

SiH polymers may thus be selected from those having the formula:

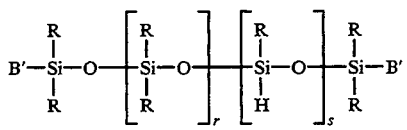

(4)

where R, r and s have the meanings given above for formula (1) and radicals B', which may be the same for each occurrence or different, are selected from radicals R and a hydrogen atom; and from those having the formula:

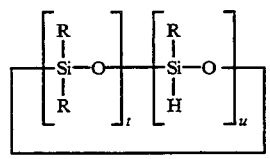

(5)

where R, t and u have the meanings given above for formula (2).

SiH polymers having formula (4) or (5) are reacted by hydrosilylation in the presence of a catalytic quantity of a platinum catalyst or an organic benzolmalonate derivative selected from those having the formula:

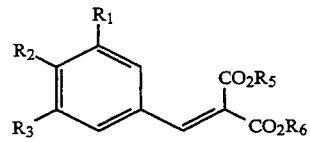

(6)

where $R_1$, $R_2$, $R_3$, $R_5$ and $R_6$ have the meanings given for formula (3) above except that radical Y is the unsaturated homologue radical Y' with the formula:

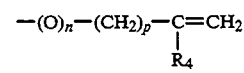

where n, p and $R_4$ have the meaning given for formula (3) above.

Certain derivatives with formula (6) where n=1 have already been described in the chemical literature, especially *J. Chem. Soc.* PERKINS TRANS (I)—1985, pp 1627-1635 and *Chem. Ber.* Vol 99—pp 1962-1965.

In general, derivatives with formula (6) can be prepared using a KNOEVENAGEL reaction, viz. condensation of an aromatic aldehyde (II) with a malonic acid ester (III) in toluene in the presence of a piperidinium acetate catalyst. Water is eliminated by azeotropy. The reaction scheme is as follows:

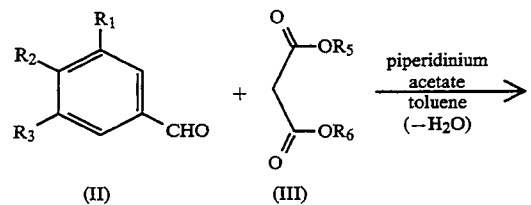

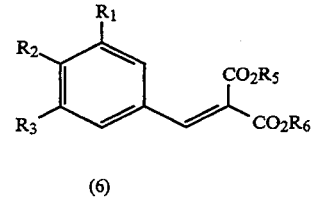

(6)

$R_1$, $R_2$, $R_3$, $R_5$ and $R_6$ having the meanings given above for formula (6).

The products are recrystallised, distilled or separated using column chromatography. Aldehydes (II), which are known compounds, may be obtained by one of the following methods:

First method

Aldehyde with formula (II) where $R_1$ represents the moiety —$(CH_2)_p$—$C(R_4)$=$CH_2$ where p=1, $R_2$ represents a hydroxyl moiety and $R_3$ has the meaning defined above for formula (6) may be obtained by the CLAISEN rearrangement of an aldehyde with formula (IV) according to the following reaction scheme:

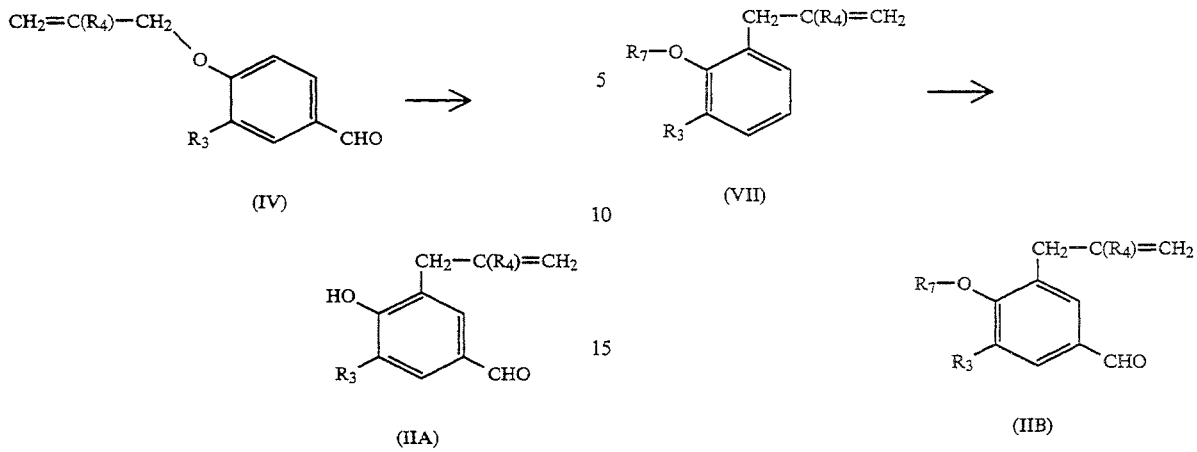

(IV) → (IIA)

(VII) → (IIB)

This rearrangement can be carried out under the conditions described by TARBELL (Organic Reactions, Vol. 2, John WILEY, New York, 1944, page 1), by heating the compound with formula (IV) to at least about 170° C., if necessary in the presence of a solvent.

Aldehyde with formula (IV) may be obtained by reaction of an alkenyl halide with formula (V) with an aldehyde with formula (VI):

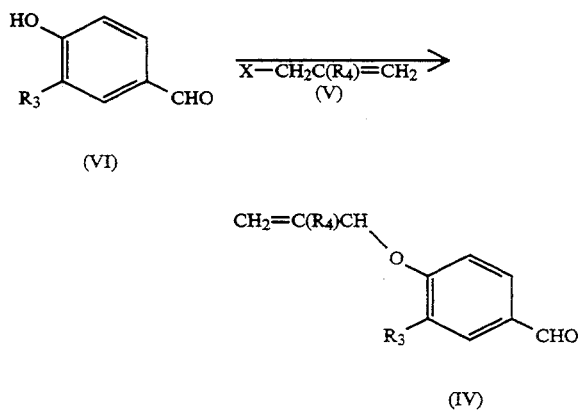

(VI) + X—CH$_2$C(R$_4$)=CH$_2$ (V) → (IV)

This reaction is carried out in the presence of a base in a solvent, for example in the presence of an alkali metal carbonate in dimethylformamide, at a temperature between room temperature and the boiling point of the solvent. Aldehyde with formula (VI) may be prepared by known methods. In the compound with formula (V), X represents a halogen atom, preferably chlorine or bromine.

Second method

Aldehyde with formula (IIB) corresponding to formula II where R$_1$ represents a —(CH$_2$)$_p$—C(R$_4$)=CH$_2$ moiety where p=1, R$_2$ represents a C$_1$-C$_6$ alkoxy moiety and R$_3$ has the meaning given above for formula (6) may be obtained by one of the two following routes:

First route

Formylation of a phenol ether with formula (VII) according to the following reaction scheme:

where R$_7$ represents a C$_1$-C$_6$ alkyl radical, R$_3$ having the meaning given above.

This reaction may, for example, be carried out by addition of the complexes formed by the action of phosphorus oxychloride on disubstituted formamides (see VILSMEIER and HAAK, Ber., 60, p 119, 1927) on compounds with formula (VII).

The phenol ether with formula (VII) can be prepared using known methods.

Second route

Compound with formula (IIA) obtained from the first method can be transformed into compound with formula (IIB) by reaction with a C$_1$-C$_6$ alkyl halide or sulphate in the presence of a base, for example in the presence of an alkali metal carbonate, in a solvent such as dimethylformamide, or in the presence of an alkali metal hydride in 1,2-dimethoxyethane, according to the following reaction scheme:

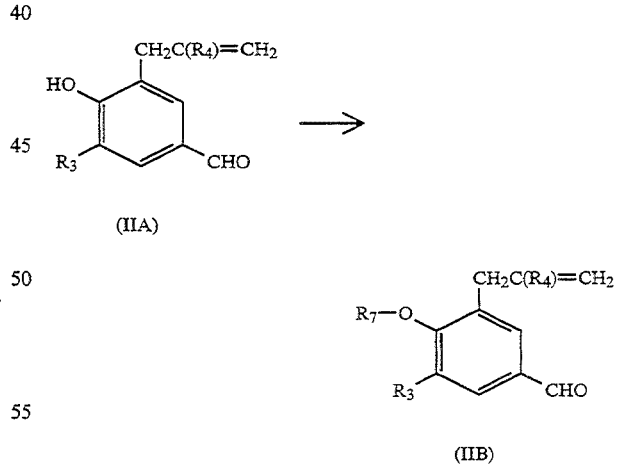

(IIA) → (IIB)

In the compound with formula (IIB), R$_7$ represents a C$_1$-C$_6$ alkyl moiety.

Third method

Aldehyde with formula (II) where R$_1$ or R$_2$ represent a —(CH$_2$)$_p$—C(R$_4$)=CH$_2$ moiety and R3 represents a hydrogen atom, a C$_1$-C$_6$ alkyl moiety or a C$_1$-C$_6$ alkoxy moiety may also be obtained by reaction of ethyl orthoformate with phenylmagnesium bromide with formula (VIII) followed by hydrolysis of the resulting acetal:

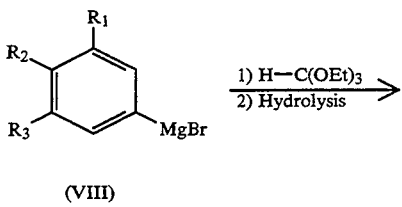

(VIII)

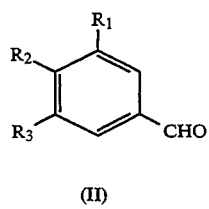

(II)

This reaction may be carried out under the conditions described by QUELET (C.R. Acad. Sci. vol. 182, p 1285 and Bull. Soc. Chim. Fr., vol. 45, p 267), for example in an inert solvent such as ethyl ether, dioxane or 1,2-dimethoxyethane, at a temperature between room temperature and the boiling point of the solvent. In compounds with formula (II) and (VIII), one of the substituents $R_1$ or $R_2$ represents the radical $-(CH_2)_p-C(R_4)=CH_2$, $R_4$ and p having the meanings defined above, and the other represents hydrogen, a $C_1-C_6$ alkyl radical or a $C_1-C_6$ alkoxy radical and $R_3$ represents hydrogen, a $C_1-C_6$ alkyl radical or a $C_1-C_6$ alkoxy radical.

Platinum catalysts used for hydrosilylation of polymers with formula (4) or (5) with the organic derivative with formula (6) are amply described in the literature. Complexes of platinum and an organic product merit particular mention. These are described in American patents U.S. Pat Nos. 3,159,601, 3,159,602 and 3,220,972 and European patents EP-A-57 459, EP-A-188 978 and EP-A-190 530. American patents U.S. Pat Nos. 3,419,593, 3,377,432 and U.S. Pat Nos. 3,814,730 describe other complexes of platinum and a vinylated organopolysiloxane.

For the reaction of the SiH polymer with formula (4) or (5) on the derivative with formula (6), the amount of platinum catalyst used comprises between 5 and 600 ppm platinum, calculated by weight of platinum metal, preferably between 10 and 200 ppm based on the weight of SiH polymer with formula (4) or (5).

The hydrosilylation reaction may take place in the dry state or using a volatile organic solvent such as toluene, heptane, xylene, tetrahydrofurane or tetrachloroethylene.

It is generally desirable to heat the reaction mixture to a temperature of 60° to 120° C. for the time necessary to complete the reaction. The SiH polymer may be added dropwise to a solution of the derivative with formula (6) in an organic solvent containing the catalyst. The SiH polymer and the derivative with formula (6) may also be added simultaneously to a suspension of the catalyst in an organic solvent.

Reaction completeness is verified by titrating residual SiH against alcoholic potash. The solvent is then eliminated, for example by distillation under reduced pressure.

The crude oil obtained can be purified, for example by passage over an absorbent silica column.

A further object of the invention is constituted by cosmetic compositions to protect the skin and hair against UV radiation, containing an effective quantity of a benzalmalonate diorganopolysiloxane having formula (1) or (2), in a cosmetically acceptable medium.

A further object of the invention is a method of protecting skin and natural or sensitised hair against solar radiation, consisting in applying to the skin or hair an effective quantity of at least one compound having formula (1) or (2) in an acceptable cosmetic support comprising at least one oily phase.

"Sensitised hair" means hair which has been permed, dyed or bleached.

A still further object of the invention is a tinted or untinted, light stable cosmetic composition comprising an effective quantity of at least one benzalmalonate diorganopolysiloxane having formula (1) or (2).

When used as a composition for protecting the human epidermis against ultraviolet radiation, the preparation may be in many of the diverse forms commonly used for this type of cosmetic composition. In particular, oily, alcoholic or oleoalcoholic lotions may be used, also emulsions such as creams or milks, oleoalcoholic, alcoholic or hydroalcoholic gels, solid sticks or aerosols.

It may contain any cosmetic additives normally used in this type of composition, such as thickeners, softeners, moisturisers, surfactants, preservatives, anti-foaming agents, perfumes, oils, waxes, lanolin, propellants, dyes and/or pigments to colour the composition itself or the skin, or any other ingredient normally used in cosmetics.

The compound with formula (1) or (2) is present in proportions of between 0.25 and 3% by weight with respect to the total weight of the protective cosmetic composition for the human epidermis.

As solubilising solvent, an oil may be used, or a wax or generally any oily body, a monoalcohol or a low polyol, or a $C_{12}-C_{15}$ alcohol benzoate or a mixture thereof. Particularly preferred monoalcohols or polyols are ethanol, isopropanol, propyleneglycol, glycerine or sorbitol.

One embodiment of the invention is an emulsion in the form of a protective cream or milk comprising, as well as the compound with formula (1) or (2), fatty alcohols, fatty acid esters in particular fatty acid triglycerides, fatty acids, lanolin, natural or synthetic oils or waxes and emulsifiers, in the presence of water.

A further embodiment is constituted by oily lotions with bases of natural or synthetic oils or waxes, lanolin and fatty acid esters, in particular fatty acid triglycerides, or by oleoalcoholic lotions with a low alcohol base such as ethanol or a glycol such as propyleneglycol and/or a polyol such as glycerine and oils, waxes and fatty acid esters such as fatty acid triglycerides.

The cosmetic composition of the invention may also be in the form of an alcoholic gel comprising one or more alcohols or low polyols such as ethanol, propyleneglycol or glycerine and a thickener such as silica. Oleoalcoholic gels further contain a natural or synthetic oil or wax.

Solid sticks are constituted by natural or synthetic waxes and oils, fatty alcohols, fatty acid esters, lanolin and other oily substances.

For aerosol type compositions, standard propellants such as alkanes, fluoroalkanes and chlorofluoroalkanes are used.

The scope of the present invention also covers sun screening cosmetic compositions containing at least one compound with formula (1) or (2) and which may contain other UV-B and/or UV-A filters.

In this case the total quantity of filters present in the sun screen composition, i.e. the compound with formula (1) or (2) and other filters if any, lies between 0.5 and 15% by weight with respect to the total sun screen composition weight.

The forms described above for the human skin protection compositions may also be used for these sun screen compositions.

When the inventive cosmetic composition is intended to protect natural or sensitised hair from UV radiation the composition may be in the form of a shampoo, lotion, gel or rinsing emulsion, for application before or after shampooing, before or after dyeing or bleaching, before or after a perm, as a styling or treating gel, brushing or setting gel or lotion, hairspray or lacquer. As well as the inventive compound the composition may contain any of the additives used in this type of composition such as surfactants, thickeners, polymers, softeners, preservatives, foam stabilisers, electrolytes, organic solvents, siliconised derivatives, oils, waxes, degreasing agents, dyes and/or pigments to colour the composition itself or the hair or any other ingredient which is normally used in hairdressing.

It contains 0.25% to 5% by weight of the compound with formula (1) or (2).

The present invention further provides a cosmetic composition containing at least one compound with formula (1) or (2) as a protective agent against ultraviolet radiation constituted as a hairdressing composition such as a hair lacquer a setting lotion, possibly for treating or untangling, a tinting shampoo, a hair dye composition, a cosmetic composition such as nail polish, a treatment cream or oil for the skin, a foundation, a lipstick, a skin care composition such as a bath oil or cream and any other cosmetic composition which, because of its ingredient may lack light stability during storage.

Such compositions contain 0.25 to 3% by weight of compound with formula (1) or (2).

The invention further envisages a method for protecting cosmetic compositions against ultraviolet radiation consisting in incorporating an effective quantity of at least one compound with formula (1) or (2) into these compositions.

The following examples illustrate the invention without limiting its scope.

EXAMPLE 1

Preparation of a random polymer of formula.

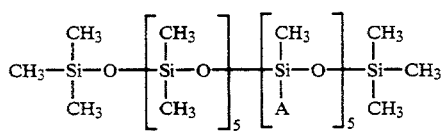

(1)

where A represents:

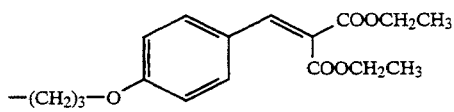

A solution in 55 ml toluene of 30 g diethyl 4-allyloxy benzalmalonate and 16 g of the random polymer having the above formula where A is an atom of hydrogen was added dropwise over one hour 30 minutes to a suspension of 5% (166 mg) platinum on carbon in dry toluene (5 ml) at 90°–100° C. under nitrogen and agitation. The temperature was maintained throughout at 100° to 105° C.

The mixture was stirred and refluxed until the SiH groups had disappeared (absence of 2 180 cm$^{-1}$ infrared band), i.e. for ten hours. It was filtered over paper, the solvent eliminated and washed twice with 80% ethanol. The oil obtained was taken up in chloroform, dried over sodium sulphate and filtered over celite to eliminate the remaining colloidal platinum. After evaporation of the solvent a pale yellow oil was obtained (weight: 36 g, yield: 78%).

UV spectrum (ethanol): λmax: 311 nm

Nuclear magnetic resonance analysis ($^1$H and $^{29}$Si) indicated that the product had the desired structure.

EXAMPLE 2

Preparation of a random polymer with formula:

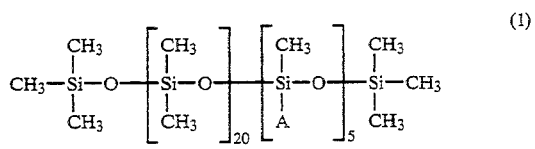

(1)

where A represents:

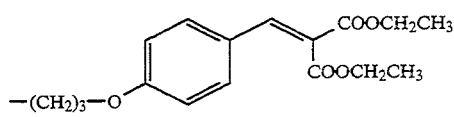

The method of example 1 was repeated using the random polymer having the above formula where A is an atom of hydrogen.

A light yellow oil was thus obtained.

UV spectrum (CHCl$_3$): λmax: 313 nm

EXAMPLE 3

Preparation of a random polymer with formula:

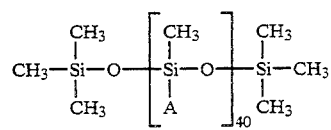

where A represents:

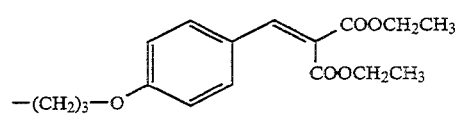

The method of example 1 was repeated starting from the random polymer with the above formula where A is a hydrogen atom.

A viscous yellow oil was obtained.

UV spectrum (CHCl$_3$): λmax: 313 nm

EXAMPLE 4

Preparation of a random polymer with formula:

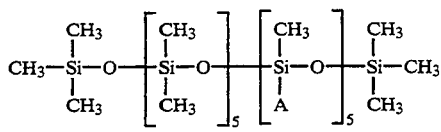

(1)

where A represents:

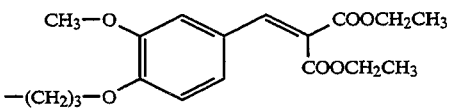

The method of example 1 was repeated starting this time with 20 g diethyl 4-allyloxy-3-methoxybenzalmalonate and 9.7 g of the random polymer with the above formula where A is a hydrogen atom.

22 g of a thick pale yellow oil was obtained (yield: 74%).

UV spectrum (CHCl$_3$): λmax$_1$: 330 nm λmax$_2$: 300 nm (shoulder)

Nuclear magnetic resonance analysis ($^1$H and $^{29}$Si) indicated that the product had the expected structure.

EXAMPLE 5

Preparation of a random polymer with formula:

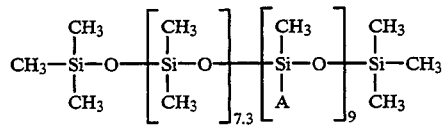

where A represents:

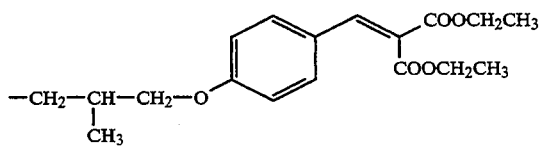

22.7 g (0.071 mole) diethyl 4-methallyloxybenzalmalonate, 33 g toluene and 14.4 l of a solution in hexane (8.45%) by weight of platinum metal) of a platinum complex prepared from chloroplatinic acid and 1,3-divinyl 1,1,3,3-tetramethyldisiloxane as described in U.S. Pat No. 3,814,730, were placed in a 3-necked flask equipped with a magnetic stirrer and a cooling column and maintained at 100° C. in an oil bath.

10 g of a random polymer with the above formula where A is an atom of hydrogen, titrating 713 meq/100 g of SiH group (meq=milliequivalent), was added over a period of one hour.

After 24 hours of reaction a transformation rate of 73% for the SiH groups was determined by titration of SiH groups against butanolic potassium.

A cloudy slightly yellow oil having an agreeable odour and very high viscosity was obtained following elimination of toluene by distillation at 100° C. under a reduced pressure of 0.66 kPa.

Proton nuclear magnetic resonance analysis ($^1$H NMR) at 360 MHz in CDCl$_3$ was carried out on a sample of the oil obtained. This showed the existence of unreacted monomer, hydrogenosilane and the structure resulting from hydrosilylation of the unsaturated methallyloxy group of the monomer, viz:

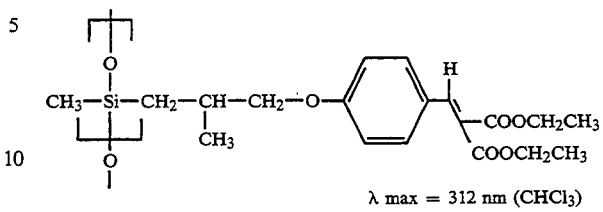

λ max = 312 nm (CHCl$_3$)

EXAMPLE 6

Example 6a : Diethyl-3-allyl-4-methoxybenzalmalonate

Preparation of a compound having general formula (6) where R$_1$ represents the radical —CH$_2$—CH=CH$_2$, R$_2$ represents the radical —OCH$_3$, R$_3$ represents a hydrogen atom and R$_5$ and R$_6$ represent the radical —C$_2$H$_5$:

Stage one: Preparation of 3-allyl-4-methoxybenzaldehyde

First method 50 g (0.308 mole) 4-allyloxybenzaldehyde was heated at 220° C. for four hours under nitrogen and with stirring. The cooled reaction mixture was taken up in dichloromethane and extracted with 5N soda. The aqueous phase was acidified with 6N hydrochloric acid and extracted with dichloromethane. The organic phase was dried and the solvent evaporated off to leave a brown-black oil. After vacuum distillation the fraction boiling between 138°-140° C. at 106 Pa was collected — 15 g (yield 30%) 3-allyl-4-hydroxybenzaldehyde (white powder, melting point=66° C.).

To this derivative (14.5 g, 0.089 mole) were successively added 30 ml N,N-dimethylformanide, 13.6 g (0.098 mole) anhydrous potassium carbonate and 11 ml (0.178 mole) methyl iodide. This mixture was heated to 60°-70° C. for three hours. The reaction mixture was poured onto iced water and extracted with diisopropyl ether. The organic phase was dried over sodium sulphate, filtered and the solvent evaporated off to obtain 3-allyl-4-methoxybenzaldehyde (pale yellow oil, 13.6 g, yield=87%).

Second method 2-allylphenol (100 g, 0.75 mole), 2 liters dry N,N-dimethylformanide and anhydrous potassium carbonate (206 g, 1.49 mole) were successively introduced into a 5 liter reaction vessel. At room temperature methyl iodide (92 ml, 1.49 mole) was added dropwise. The vessel was left for four hours at 38° C. The reaction mixture was then poured onto iced water and extracted with dichloromethane.

The organic phase was washed with water and dried. After evaporation of the solvent and vacuum distillation, the fraction distilling at 110° C. at 5 000 Pa was collected: 2-allylanisole (colourless liquid, 46 g, yield=42%). N,N-dimethylformanide (75 ml, 0.98 mole) was placed in a 500 ml reactor. Added to this, whilst cooling to about 5° C., was phosphorus oxychloride (26 ml, 0.28 mole). The mixture was held at 10° C. for one hour then the above derivative (41.5 g, 0.28 mole) added dropwise. The temperature was steadily raised to 100° C. over a period of one hour and the reaction mixture maintained at this temperature for ten hours. The cooled mixture was poured onto iced water and extracted with diisopropyl ether. The organic phases were washed with water, dried over sodium sulphate, filtered and the solvent evaporated off to leave a crude product (31 g) which was purified by chromatography on silica 60 (eluent: 50/50 toluene/hexane) to obtain a fraction (4.5 g) of 3-allyl-4-methoxybenzaldehyde identical to that obtained by the first method.

Stage two: Preparation of diethyl 3-allyl-4-methoxy-benzalmalonate

A Dean Stark apparatus was used to reflux under nitrogen a mixture of the above derivative (10 g, 0.057 mole), diethyl malonate, (9.09 g, 0.057 mole), toluene (15 ml), acetic acid (0.36 ml) and piperidine (0.68 ml). After five hours of heating, 1 ml of water was recovered. After cooling, the toluene phase was washed with water, dried and the solvent distilled. An orange oil was obtained which crystallised. This was recrystallised from diisopropyl ether and animal black. White crystals of diethyl 3-allyl-4-methoxybenzalmalonate (12.7 g, yield=70%) were obtained having the following characteristics:

melting point: 69° C. $^1$H NMR spectrum (CDCl$_3$): agreed with expected structure UV spectrum (CHCl$_3$): λmax: 318 nm ε: 24450 Elemental analysis: Calculated: C 67.91; H 6.97; O 25.13 Found : C 68.04; H 6.89; O 25.23

Example 6b

Preparation of a random polymer with formula:

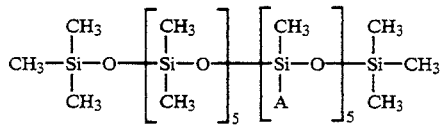

wherein A represents:

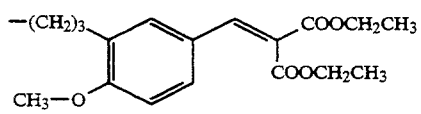

A solution in toluene (20 ml) of diethyl 3-allyl-4-methoxybenzalmalonate (10 g, 31.4 meq) and a random polymer having the above formula where A is a hydrogen atom (4.60 g, 31.4 meq of SiH) was added dropwise over a period of one hour 30 minutes to a stirred suspension of 5% platinum on carbon (55 mg) in dry toluene (5 ml) at 90°-100° C. under nitrogen. The temperature was maintained between 100° and 105° C.

The mixture was stirred and refluxed until the SiH groups had disappeared (absence of 2 180 cm$^{-1}$ band in the infrared), i.e. for eight hours. The mixture was filtered over paper, the solvent eliminated and then washed twice with 80% ethanol. The pale yellow oil obtained was taken up in dichloromethane, dried over sodium sulphate and passed over a bed of silica 60.

Following evaporation of the solvent a viscous pale yellow oil was obtained (5.3 g, yield=36%).

$^1$H NMR spectrum (CDCl$_3$) : agreed with formula, $^{29}$Si NMR spectrum (CDCl$_3$): agreed with formula, UV spectrum (CHCl$_3$) : λmax: 318 nm

EXAMPLE 7

Example 7a:

Diethyl-3-allyl-4,5-dimethoxybenzalmalonate

Preparation of a compound with general formula (6) wherein R$_1$ represents the —CH$_2$—CH=CH$_2$ radical, R$_2$ and R$_3$ represents the —OCH$_3$ radical and R$_5$ and R$_6$ represent the —C2H$_5$ radical.

Stage one 4-allyloxy-3-methoxybenzaldehyde (62.5 g, 0.325 mole) was heated to 180° C. and stirred for six hours 30 minutes, then cooled. The brown solid was taken up in dichloromethane and extracted with 5% soda. The aqueous phase was acidified with 3N hydrochloric acid. The solid obtained was filtered and recrystallised from a mixture of ethanol and water (40/60). 3-allyl-4-hydroxy-5-methoxybenzaldehyde was obtained (light beige powder, 62.5 g, yield=71%, melting point=8-3°-84° C.).

Stage two

The above derivative (34 g, 0.18 mole) was introduced into a reactor followed successively by dimethylformanide (500 ml), potassium carbonate (49 g, 0.35 mole) and methyl iodide (50 g, 0.35 mole). The temperature was maintained at 40° C. for three hours. The reaction mixture was plunged into iced water and the oil formed extracted with dichloromethane. Following washing, drying and evaporation of the solvent, a light brown oil was obtained which was passed over a bed of silica 60 to give a pale yellow oil, 3-allyl-4,5-dimethoxybenzaldehyde (34.3 g, yield=92%).

Stage three:

Using a Dean Stark apparatus, the following were refluxed together for seven hours: the above derivative (15 g, 0.073 mole), diethyl malonate (11.7 g, 0.073 mole), toluene (18 ml), acetic acid (0.46 ml) and piperidine (0.87 ml). After cooling, the toluene phase was washed with water, dried and the solvent distilled off. The pale orange oil obtained (24.5 g, yield: 96%) was crystallised from a diisopropyl ether/hexane mixture (50/50) to produce white crystal of diethyl 3-allyl-4,5-dimethoxybenzalmalonate (14.2 1 g, yield: 56%) having the following characteristics:

Melting point: 43°-44° C., $^1$H NMR spectrum (CDCl$_3$): agrees with expected formula, UV spectrum (CHCl$_3$): λmax$_1$=303 nm ε=15700 λmax$_2$=325 nm ε=12830 (shoulder) Elemental analysis: Calculated: C 65.50; H 6.94; O 27.55 Found: C 65.33; H 6.91; O 27.78

Example 7b

Preparation of a random polymer with formula:

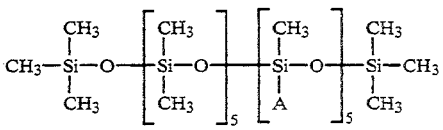

where A represents:

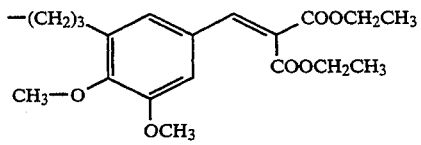       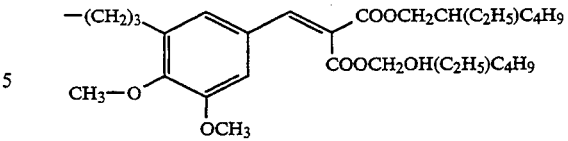

A solution of diethyl 3-allyl-4,5-dimethoxybenzalmalonate (10 g, 28.7 meq) and the above random polymer where A is a hydrogen atom (4.55 g, 28 meq SiH) in toluene (30 ml) was added dropwise over one hour 30 minutes to a stirred suspension of 5% platinum on carbon (106 mg) in dry toluene (5 ml) at 90°–100° C., under nitrogen. The temperature was maintained between 100° and 105° C. The mixture was stirred and refluxed until the SiH groups had disappeared (absence of 2 180 cm$^{-1}$ band in the infrared), viz. 12 hours. It was filtered over paper, the solvent eliminated and then washed twice with ethanol 80%. The pale yellow oil thus obtained was taken up in dichloromethane, dried over sodium sulphate and passed over a bed of silica 60. Following evaporation of the solvent a viscous pale yellow oil was obtained (10.6 g, yield: 73%).

$^1$H NMR spectrum (CDCl$_3$): agreed with formula, $^{29}$SiH NMR spectrum (CDCl$_3$): agreed with formula, UV spectrum (CHCl$_3$): λmax: 304 nm

EXAMPLE 8

Example 8a:
di-(2ethylhexyl)-3-allyl-4,5-dimethoxybenzalmalonate

Preparation of a compound of general formula (6) where R$_1$ represents radical —CH$_2$—CH=CH$_2$, R$_2$ and R$_3$ represent the radical —OCH$_3$ and R$_5$ and R$_6$ represent the radical —CH$_2$CH(C$_2$H$_5$)C$_4$H$_9$.

A Dean Stark apparatus was used to reflux the following mixture for five hours: 3-allyl-4,5-dimethoxybenzaldehyde (10.3 g, 0.05 mole) di-2-ethylhexylmalonate (16.4 g, 0.05 mole), toluene (20 ml), acetic acid (0.41. ml) and piperidine (0.77 ml). After cooling, washing the toluene phase with water, drying and evaporation of the solvent, an orange oil was obtained which was purified by chromatography on a column of silica 60 (eluent: heptane/ethyl acetate 90/10) to give di-(2-ethylhexyl)3-allyl-4,5-dimethoxybenzalmalonate (colourless oil, 15 g, yield=64%) with the following characteristics:

$^1$H NMR spectrum (CDCl$_3$): agreed with expected formula, UV spectrum (CHCl$_3$): λmax$_1$=303 nm ε=15500 λmax$_2$=320 nm ε=13430 (shoulder) Elemental analysis: Calculated: C 72.06; H 9.36; O 18.58 Found: C 72.09; H 9.44; O 18.69

Example 8b

Preparation of a random polymer with formula:

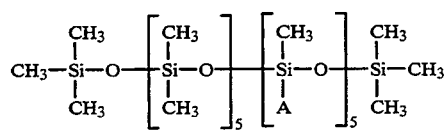

where A represents:

A solution in toluene (30 ml) of di-(2-ethylhexyl) 3-allyl-4,5-dimethoxybenzalmalonate (10 g, 19.3 meq) and the random polymer with the above formula where A is an atom of hydrogen (2.86 g, 17.6 meq SiH) was added dropwise over a period o f one hour 30 minutes to a stirred suspension of 5% platinum on carbon (80 mg) in dry toluene (5 ml ) at 90°–100° C. under nitrogen. The temperature was maintained throughout between 100 ° and 105° C. The stirring and refluxing was maintained until the SiH groups had disappeared (absence of 2 180 cm$^{-1}$ in infrared band), viz. 12 hours. It was filtered through paper, the solvent eliminated and then washed twice with 80% ethanol. The pale yellow oil obtained was taken up in dichloromethane, dried over sodium sulphate and passed over a bed of silica 60. After evaporation of the solvent a viscous pale yellow oil was obtained (5.1 g, yield=43%).

$^1$H NMR spectrum (CDCl$_3$): agreed with formula, $^{29}$SiH NMR spectrum (CDCl$_3$): agreed with formula, UV spectrum (CHCl$_3$): λmax: 305 nm

EXAMPLE 9

Example 9a:
diethyl-3-allyl-4-butoxy-5-methoxybenzalmalonate

Preparation of a compound with general formula (6) where R$_1$ represents the radical —CH$_2$CH=CH$_2$, R$_2$ represents the radical OC$_4$H$_9$, R$_3$ represents the radical —OCH$_3$ and R$_5$ and R$_6$ represent the radical —C$_2$H$_5$.

Stage one

A mixture of 3-allyl-4-hydroxy-5-methoxybenzaldehyde (10.25 g, 0.053 mole), dimethylformanide (150 ml), potassium carbonate (8.29 g, 0.06 mole) and 1-bromobutane (8.22 g, 0.06 mole) was maintained at 40°–45° C. for three hours. The reaction mixture was plunged into iced water and the oil formed extracted with dichloromethane. After washing with water, drying and evaporation of the solvent, a brown oil was obtained which was passed through a bed of silica 60 to give a pale yellow oil, 3-allyl-4-butoxy-5-methoxybenzaldehyde (13 g, yield=91%).

Stage two

A mixture of the following was refluxed in a Dean Stark apparatus for seven hours: the above derivative (10.2 g, 0.041 mole), diethyl malonate (7 g, 0.041 mole), toluene (12 ml), acetic acid (0.26 ml) and piperidine (0.49 ml). Diethyl 3-allyl-4-butoxy-5-methoxybenzalmalonate (colourless oil, 10 g, yield=67%) was obtained using the same method as in example 8a. It had the following characteristics:

$^1$H NMR spectrum (CDCl$_3$): agreed with expected formula, UV spectrum (CHCl$_3$): λmax$_1$=305 nm ε=15500 λmax$_2$=325 nm ε=13530 (shoulder) Elemental analysis: Calculated: C 67.67; H 7.74; O 24.58 Found: C 67.87; H 7.83; O 24.44

Example 9b

Preparation of a random polymer with formula:

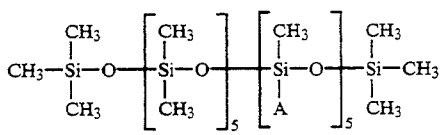

wherein A represents:

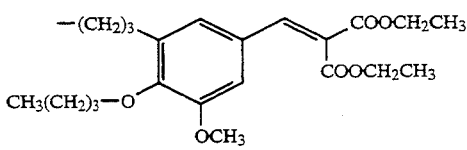

A solution in toluene (20 ml) of diethyl 3-allyl-4-butoxy-5-methoxybenzalmalonate (8.2 g, 21 meq) and a random polymer having the above formula where A is an atom of hydrogen (3.24 g, 19.9 meq SiH) was added dropwise over one hour 30 minutes to a stirred suspension of 5% platinum on carbon (60 mg) in dry toluene (5 ml) at 90°–100° C. under nitrogen. The temperature was maintained throughout between 100° and 105° C. The mixture was stirred and refluxed until the SiH groups had disappeared (absence of 2 180 cm$^{-1}$ band in the infrared), viz. ten hours. It was filtered over paper, the solvent eliminated and washed twice with 80% ethanol. The pale yellow oil obtained was taken up in dichloromethane, dried over sodium sulphate and passed through a silica 60 bed. After evaporation of the solvent a colourless viscous oil (4.7 g, yield=43%) was obtained.

$^1$H NMR spectrum (CDCl$_3$): agreed with formula,
$^{29}$SiH NMR spectrum (CDCl$_3$): agreed with formula,
UV spectrum (CHCl$_3$): A max$_1$ =306 nm λmax$_2$=325 nm

EXAMPLES OF USE

Example A: oil-in-water emulsion for the protection of human skin

| | |
|---|---|
| Compound from example 4 | 2.0 g |
| Oxyethylenated cetylstearyl acid, (C$_{16}$/C$_{18}$-35/65) (15 O.E.)("MERGITAL CS15" from HENKEL) | 3.0 g |
| Glycerol monostearate | 4.8 g |
| Myristic alcohol | 4.5 g |
| Benzoate of C$_{12}$/C$_{15}$ alcohols ("FINSOLV TN" from WITCO) | 18.0 g |
| Propylene glycol | 6.0 g |
| Preservative | 0.2 g |
| Perfume | 0.6 g |
| Demineralised water qsp | 100 g |

The oily substances and emulsifiers were heated to about 80°–85° C. and the compound from example 4 added. Alternatively the water containing the hydrosoluble compounds was heated to 80°–85° C. and the oily phase added to the aqueous phase. After ten minutes brisk stirring the mixture was allowed to cool under moderate stirring, then the perfume and preservative added.

Example B: oil-in-water sun screen emulsion

This was similar to example A but contained 2.0 g of the compound from example 6 in place of the compound from example 4.

Example C: oil-in-water sun screen emulsion

| | |
|---|---|
| Compound from example 3 | 2.0 g |
| 2-hydroxy-4-methoxybenzophenone | 1.0 g |
| Liquid lanolin | 7.0 g |
| Triglycerides of myristic/palmitic/stearic acids ("NESATOL" from VEVY) | 5.0 g |
| Oxyethylenated oleic triglycerides ("LUBRAFIL M1969 CS" from GATTEFOSSE) | 2.5 g |
| Mixture of glycerol monostrearate and stearate of polyethylene glycol (100 OE) ("ARLACEL 165" from SEPPIC) | 5.0 g |
| Stearyl alcohol | 1.0 g |
| Stearic acid | 2.5 g |
| Mixture of cetyl phosphate and the monocetyl phosphate of diethanolamine ("AMPHISOL NP" from GIVAUDAN) | 0.5 g |
| Benzoates of C$_{12}$/C$_{15}$ alcohols ("FINSOLV TN" from WITCO) | 9.0 g |
| Triethanolamine | 0.2 g |
| Preservative | 0.4 g |
| Perfume | 0.6 g |
| Demineralised water qsp | 100 g |

This emulsion was prepared as described for example A.

Example D: oil-in-water sun screen emulsion

| | |
|---|---|
| Compound from example 1 | 3.5 g |
| Mixture of cetylstearyl alcohol and oxyethylenated (33 moles OE) cetylstearyl alcohol ("SINNOWAX AO" from HENKEL) | 7.0 g |
| Glycerol monostearate | 2.0 g |
| Cetyl alcohol | 1.3 g |
| Propylene glycol | 10.0 g |
| Preservative | 0.2 g |
| Perfume | 0.6 g |
| Benzoates of C$_{12}$/C$_{15}$ alcohols ("FINSOLV TN" from WITCO) | 15.0 g |
| Demineralised water qsp | 100 g |

This emulsion was prepared as described for example A.

Example E: sun screen stick

| | |
|---|---|
| Compound from example 4 | 5.0 g |
| Hydrocarbonated mineral wax | 20.0 g |
| Beeswax | 7.0 g |
| Oleic alcohol | 12.0 g |
| Hydrogenated lanolin | 8.0 g |
| Liquid lanolin | 8.0 g |
| Carnauba wax | 1.0 g |
| Benzoate of alcohols C$_{12}$/C$_{15}$ ("FINSOLV TN" from WITCO) | 20.0 g |
| Perfume | 1.2 g |
| Vaseline oil qsp | 100 g |

Example F: sun screen stick

This was similar to example E but using 5.0 g of the compound from example 9 in place of the compound from example 4.

Example G: sun screen oil

| | |
|---|---|
| Compound from example 3 | 3.5 g |
| Sweet almond oil | 3.0 g |
| Perfume | 1.2 g |
| Benzoate of alcohols C$_{12}$/C$_{15}$ ("FINSOLV TN" from WITCO) qsp | 100 g |

Example H: sun screen oil

This was similar to example G but replacing the compound from example 3 with the compound from example 8.

Example I: water-in-oil sun screen emulsion

| | |
|---|---|
| Compound from example 4 | 3.0 g |
| Mixture of diorganopolysiloxane grafted with cetyl and polyethoxy-polypropoxy-propyloxy groups, polyglycerol oleate and hexyl laurate, denominated in the CTFA dictionary as cetyldimethicone copolyol/cetyldimethicone/polyglycerol-3-oleate/hexyl laurate ("ABIL WS 08" from GOLDSCHMIDT) | 5.0 g |
| Benzoate of alcohols $C_{12}/C_{15}$ ("FINSOLV TN" from WITCO) | 12.0 g |
| Vaseline | 2.0 g |
| Beeswax | 2.5 g |
| Glycerine | 2.0 g |
| Sodium chloride | 2.0 g |
| Preservative | 0.2 g |
| Perfume | 0.6 g |
| Demineralised water | 100 g |

This emulsion was prepared as described for example A except that the aqueous phase was added to the oily phase.

Example J: oil-in-water sun screen emulsion

| | |
|---|---|
| Compound from example 5 | 1.7 g |
| Compound from example 7 | 1.8 g |
| Mixture of cetylstearyl alcohol and oxyethylenated (33 moles OE) cetylstearyl alcohol ("SINNOWAX AO" from HENKEL) | 7.0 g |
| Glycerol monostearate | 2.0 g |
| Cetyl alcohol | 1.3 g |
| Propylene glycol | 10.0 g |
| Benzoates of $C_{12}/C_{15}$ alcohols ("FINSOLV TN" from WITCO) | 15.0 g |
| Preservative | 0.2 g |
| Demineralised water qsp | 100 g |

This emulsion was prepared as described for example A.

Example K: oil-in-water sun screen emulsion

| | |
|---|---|
| Compound from example 2 | 5.0 g |
| Mixture of cetylstearyl alcohol and oxyethylenated (33 moles OE) cetylstearyl alcohol ("SINNOWAX AO" from HENKEL) | 7.0 g |
| Glycerol monostearate | 2.0 g |
| Propylene glycol | 10.0 g |
| Cetyl alcohol | 1.3 g |
| Benzoates of $C_{12}/C_{15}$ alcohols ("FINSOLV TN" from WITCO) | 15.0 g |
| Preservative | 0.2 g |
| Demineralised water qsp | 100 g |

This emulsion was prepared as described in example A.

The compositions of examples A to K are intended for application to the skin to protect it from UV radiation.

Example L: protective oil for the hair

| | |
|---|---|
| Compound from example 1 | 1.0 g |
| Absolute ethanol | 50 g |
| 1,3,3,5-tetramethyl-1,1,5,5-trisiloxane | 65 g |
| ("Huile 763" from RHONE POULENC) | |

This product is in the form of a clear oil.

When applied to dry hair this oil makes it smooth and shiny whilst simultaneously protecting it from ultraviolet radiation.

We claim:

1. A cosmetic composition which comprises in a cosmetically acceptable support at least one cosmetic additive selected from the group consisting of thickeners, softeners, moisturizers, surfactants, preservatives, antifoaming agents, perfumes, oils, waxes, lanoline, low monoalcohols and polyols, $C_{12}$–$C_{15}$ alcohol benzoates, propellants, dyes and pigments and at least one benzalmalonate polydimethylsiloxane selected from those having the formula:

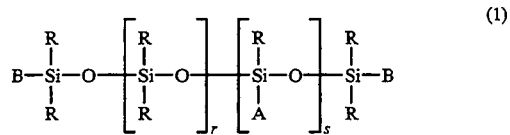 (1)

wherein:
R may be the same for each occurrence or different and is selected from $C_1$–$C_{10}$ alkyl radicals, phenyl radicals and 3,3,3-trifluoropropyl radicals, at least 80% by number of the R radicals being methyl radicals,
B may be the same for each occurrence or different and is selected from radicals R and A,
r is a number between 0 and 200 inclusive,
s is a number between 0 and 50 inclusive and if s is at least one of the two B radicals is A;
and from those having the formula:

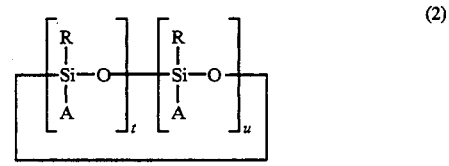 (2)

wherein:
R has the meaning defined for formula (1),
u is a number between 1 and 20 inclusive,
t is a number between 0 and 20 inclusive,
t+u is greater than or equal to 3;
and wherein in both formulae the symbol A denotes a radical having the formula:

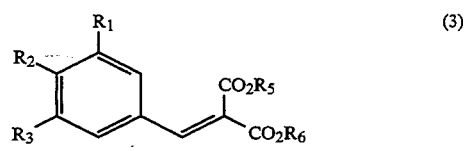 (3)

wherein:
$R_1$ and $R_2$ are selected from a hydrogen atom, a hydroxyl radical, a trimethylsiloxy radical, a $C_1$–$C_6$ alkoxy radical and a divalent group Y with the formula:

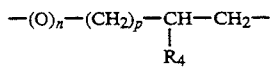

wherein:
n is 0 or 1,
p is a whole number between 1 and 10 inclusive, and $R_4$ is selected from a hydrogen atom and a $C_1$-$C_4$ alkyl radical, one of the two radicals $R_1$ and $R_2$ necessarily representing group Y,
$R_3$ represents a hydrogen atom, a $C_1$-$C_6$ alkyl radical or a $C_1$-$C_6$ alkoxy radical,
$R_5$ and $R_6$ may be identical or different and represent a $C_1$-$C_8$ alkyl radical,
said composition being selected from the group consisting of a protective composition for the human skin containing 0.25 to 3% by weight of said benzalmalonate diorganopolysiloxane, a sunscreen composition containing 0.5 to 15% by weight of said benzalmalonate diorganopolysiloxane, a composition for application to the hair in the form of a shampoo, lotion, rinsing gel, or emulsion containing 0.25 to 5% by weight of said benzalmalonate diorganopolysiloxane, and a hairdressing composition containing 0.25 to 3% by weight of said benzalmalonate diorganopolysiloxane.

2. A cosmetic composition according to claim 1, which comprises a random or block benzalmalonate diorganopolysiloxane with formula (1) or (2) having at least one of the following characteristics:
R is methyl,
B is methyl,
$R_1$ is H or Y,
$R_2$ is Y, methoxy or butoxy,
$R_3$ is H or methoxy,
n=0 or 1,
p=1,
$R_4$ is H or methyl,
$R_5$ and $R_6$ are ethyl or 2-ethylhexyl,
r is between 5 and 20 inclusive,
s is between 2 and 15 inclusive,
t+u is between 3 and 10 inclusive.

3. A cosmetic composition according to claim 1, which comprises a benzalmalonate polydimethylsiloxane with formula (1) where R and B represent methyl, r=5, s=5, $R_1$ is H, $R_2$ is Y with n=1, p=1 and $R_4$ is H, $R_3$ is H or methoxy and R5 and $R_6$ are ethyl.

4. A cosmetic composition according to claim 1 which comprises a benzalmalonate polydimethylsiloxane with formula (1) where R and B represent methyl, r=20, s=5, $R_1$ is H, $R_2$ is Y with n=1, p=1 and $R_4$ is H, $R_3$ is H and $R_5$ and $R_6$ are ethyl.

5. A cosmetic composition according to claim 1, which comprises a benzalmalonate polydimethylsilonxane with formula (1) where R and B represent methyl, r=0, s=40, $R_1$ is H, $R_2$ is Y with n=1, p=1 and $R_4$ is H, $R_3$ is H and $R_5$ and $R_6$ are ethyl.

6. A cosmetic composition according to claim 1 which comprises a benzalmalonate polydimethylsiloxane with formula (1) where R and B represent methyl, r=7.3, s=9, $R_1$ is H, $R_2$ is Y with n=1, p=1 and $R_4$ is $CH_3$, $R_3$ is H and $R_5$ and $R_6$ are ethyl.

7. A cosmetic composition according to claim 1, which comprises a benzalmalonate polydimethylsiloxane with formula (1) where R and B represent methyl, r=5, s=5, $R_1$ is Y with n=0, p=1 and $R_4$ is H, $R_2$ is methoxy, $R_3$ is H or methoxy and $R_5$ and $R_6$ are ethyl.

8. A cosmetic composition according to claim 1 which comprises a benzalmalonate polydimethylsiloxane with formula (1) where R and B represent methyl, r=5, s=5, $R_1$ is Y, with n=0, p=1 and $R_4$ is H, $R_2$ is methoxy, $R_3$ is methoxy and $R_5$ and $R_6$ are 2-ethylhexyl.

9. A cosmetic composition according to claim 1 which comprises a benzalmalonate polydimethylsiloxane with formula (1) where R and B represent methyl, r=5, s=5, $R_1$ is Y, with n=0, p=1 and $R_4$ is H, $R_2$ is butoxy, $R_3$ is methoxy and $R_5$ and $R_6$ are ethyl.

10. A cosmetic composition according to claim 1 which is in the form of an oily, alcoholic or oleoalcoholic lotion, emulsion, oleoalcoholic, alcoholic or hydroalcoholic gel, solid stick, spray or aerosol.

11. A sun screen cosmetic composition according to claim 1 which further contains a UV-B UV-A radiation filter agent.

12. A method for protecting skin and natural or sensitized hair against ultraviolet radiation which consists in applying to the skin or hair an effective quantity of a cosmetic composition containing as a UV radiation filter for wavelengths between 280 and 360 nm at least one benzalmalonate polydimethylsiloxane selected from those having the formula:

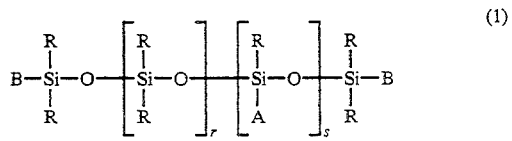

wherein:
R may be the same for each occurrence or different and is selected from $C_1$-$C_{10}$ alkyl radicals, phenyl radicals and 3,3,3-trifluoropropyl radicals, at least 80% by number of the R radicals being methyl radicals,
B may be the same for each occurrence or different and is selected from radicals R and A,
r is a number between 0 and 200 inclusive,
s is a number between 0 and 50 inclusive and if s is 0 at least one of the two B radicals is A;
and from those having the formula:

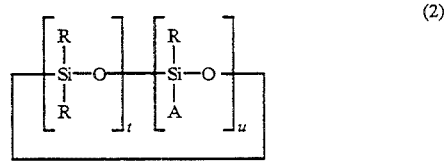

wherein:
R has the meaning defined for formula (1),
u is a number between 1 and 20 inclusive,
t is a number between 0 and 20 inclusive,
t+u is greater than or equal to 3;
and wherein in both formulae the symbol A denotes a radical having the formula:

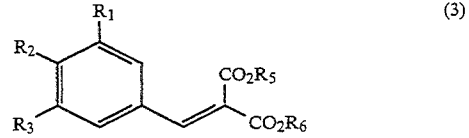

wherein:

$R_1$ and $R_2$ are selected from a hydrogen atom, a hydroxyl radical, a trimethylsiloxy radical, a $C_1$–$C_6$ alkyl radical, a $C_1$–$C_6$ alkoxy radical and a divalent group Y with the formula:

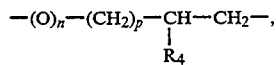

wherein:
n is 0 or 1,
p is a whole number between 1 and 10 inclusive, and $R_4$ is selected from a hydrogen atom and a $C_1$–$C_4$ alkyl radical, one of the two radicals $R_1$ and $R_2$ necessarily representing group Y,
$R_3$ represents a hydrogen atom, a $C_1$–$C_6$ alkyl radical or a $C_1$–$C_6$ alkoxy radical.

13. A method of protecting a cosmetic composition against ultraviolet radiation which consists in incorporating into said composition an effective quantity for filtering UV radiation for wavelengths between 280 and 360 nm of at least one benzalmalonate polydimethylsiloxane selected from those having the formula:

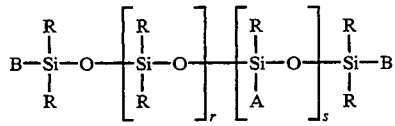 (1)

wherein:
R may be the same for each occurrence or different and is selected from $C_1$–$C_{10}$ alkyl radicals, phenyl radicals and 3,3,3-trifluoropropyl radicals, at least 80% by number of the R radicals being methyl radicals,
B may be the same for each occurrence or different and is selected from radicals R and A,
r is a number between 0 and 200 inclusive,
s is a number between 0 and 50 inclusive and is s is 0 at least one of the two B radicals is A;
and from those having the formula:

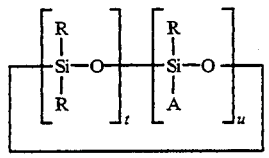 (2)

wherein:
R has the meaning defined for formula (1),
u is a number between 1 and 20 inclusive,
t is a number between 0 and 20 inclusive,
t+u is greater than or equal to 3;
and wherein in both formulae the symbol A denotes a radical having the formula:

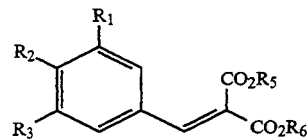 (3)

wherein:
$R_1$ and $R_2$ are selected from a hydrogen atom, a hydroxyl radical, a trimethylsiloxy radical, a $C_1$–$C_6$ alkyl radical, a $C_1$–$C_6$ alkoxy radical and a divalent group Y with the formula:

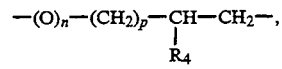

wherein:
n is 0 or 1,
p is a whole number between 1 and 10 inclusive, and $R_4$ is selected from a hydrogen atom and a $C_1$–$C_4$ alkyl radical, one of the two radicals $R_1$ and $R_2$ necessarily representing group Y,
$R_3$ represents a hydrogen atom, a $C_1$–$C_6$ alkyl radical or a $C_1$–$C_6$ alkoxy radical;
$R_5$ and $R_6$ may be identical or different and represent a $C_1$–$C_8$ alkyl radical.

* * * * *

UNITED STATES PATENT AND TRADEMARK OFFICE
CERTIFICATE OF CORRECTION

PATENT NO. : 5,415,854

DATED : May 16, 1995

INVENTORS : Forestier et al.

Page 1 of 2

It is certified that error appears in the above-identified patent and that said Letters Patent is hereby corrected as shown below:

Column 5, line 39, "$CH_2=C(R_4)CH...$" should be -- $CH_2=C(R_4)CH_2...$ --.

Column 6, line 64, "and R3 represents" should be -- and $R_3$ represents --.

Column 9, line 36, "its ingredient may" should be -- its ingredients, may --.

Column 11, line 47, "14.4 l" should be -- 14.4 $\mu l$ --.

Column 12, line 38, "N,N-dimethylformanide" should be -- N,N-dimethylformamide --.

Column 12, line 48-49, "N,N-dimethylformanide" should be -- N,N-dimethylformamide --.

Column 12, line 60, "N,N-dimethylformanide" should be -- N,N-dimethylformamide --.

Column 14, line 9, "-C2H$_5$" should be -- -$C_2H_5$ --.

Column 14, lines 26-27, "dimethylformanide" should be -- dimethylformamide --.

Column 14, line 49, "(14.2 1 g," should be -- (14.2 g, --.

Column 15, line 27, "$^{29}SiH$" should be -- $^{29}Si$ --.

Column 15, line 33, "di-(2ethylhexyl)-" should be -- di-(2-ethylhexyl)- --.

UNITED STATES PATENT AND TRADEMARK OFFICE
CERTIFICATE OF CORRECTION

PATENT NO. : 5,415,854

DATED : May 16, 1995

INVENTORS : Forestier et al.

It is certified that error appears in the above-identified patent and that said Letters Patent is hereby corrected as shown below:

Column 15, line 41, "di-2-ethylhexylmalonate" should be -- di-(2-ethylhexyl)malonate --.

Column 16, line 4, "COOCH$_2$OH..." should be -- COOCH$_2$CH... --.

Column 16, line 36, "OC$_4$H$_9$," should be -- -OC$_4$H$_9$, --.

Column 16, line 41, "dimethylformanide" should be -- dimethylformamide --.

Column 17, line 37, "A max," should be -- $\lambda$naxm --.

Column 22, line 16, "UV-B UV-A" should be -- UV-B or UV-A --.

Signed and Sealed this

Twenty-first Day of May, 1996

Attest:

BRUCE LEHMAN

*Attesting Officer*   *Commissioner of Patents and Trademarks*